United States Patent
Chen et al.

(10) Patent No.: US 12,379,356 B2
(45) Date of Patent: Aug. 5, 2025

(54) METHOD FOR DETERMINING DEGREE OF DONENESS OF STURGEON MEAT BASED ON FLAVOR FINGERPRINTING AND PARTIAL LEAST SQUARES (PLS) REGRESSION

(71) Applicant: ZHEJIANG GONGSHANG UNIVERSITY, Hangzhou (CN)

(72) Inventors: YueWen Chen, Hangzhou (CN); ShiKe Shen, Hangzhou (CN); XiuPing Dong, Hangzhou (CN); DanLi Jin, Hangzhou (CN); FeiJian Liu, Hangzhou (CN); WenQiang Cai, Hangzhou (CN); Jianling Wei, Hangzhou (CN); ShaoTian Ren, Hangzhou (CN); TingTing Chai, Hangzhou (CN)

(73) Assignee: ZHEJIANG GONGSHANG UNIVERSITY, Hangzhou (CN)

( * ) Notice: Subject to any disclaimer, the term of this patent is extended or adjusted under 35 U.S.C. 154(b) by 545 days.

(21) Appl. No.: 17/918,336

(22) PCT Filed: Mar. 18, 2022

(86) PCT No.: PCT/CN2022/081677
§ 371 (c)(1),
(2) Date: Oct. 12, 2022

(87) PCT Pub. No.: WO2022/206427
PCT Pub. Date: Oct. 6, 2022

(65) Prior Publication Data
US 2023/0304976 A1    Sep. 28, 2023

(30) Foreign Application Priority Data
Apr. 1, 2021  (CN) .......................... 202110359191.0

(51) Int. Cl.
*G01N 30/00* (2006.01)
*G01N 30/06* (2006.01)
*G01N 30/86* (2006.01)

(52) U.S. Cl.
CPC ......... *G01N 30/8686* (2013.01); *G01N 30/06* (2013.01)

(58) Field of Classification Search
CPC .......................... G01N 30/8686; G01N 30/06
See application file for complete search history.

(56) References Cited

FOREIGN PATENT DOCUMENTS

| CN | 105092755 A | * | 11/2015 | ............. G01N 30/06 |
| CN | 107748217 A | * | 3/2018 | ............. G01N 30/06 |

(Continued)

OTHER PUBLICATIONS

Bai Shuang, et al., Analysis of volatile flavor compounds in different stages of stir-frying of industrial semi-finished products beef sao zi, Transactions of the Chinese Society of Agricultural Engineering, 2020, pp. 290-297, vol. 36, No. 14.

(Continued)

*Primary Examiner* — Steven N Leff
(74) *Attorney, Agent, or Firm* — Bayramoglu Law Offices LLC

(57) ABSTRACT

A method for determining a degree of doneness of a sturgeon meat based on flavor fingerprinting and a partial least squares (PLS) regression is provided. The method determines the degree of doneness of a sturgeon meat sample and predicts a flavor characteristic based on gas chromatography-ion mobility spectrometry (GC-IMS) data and a linear regression equation of the sturgeon meat sample. The method includes conducting headspace (solid-phase) microextraction of sturgeon meat samples with different degrees of doneness, conducting a qualitative analysis by gas chromatography-mass spectrometry (GC-MS), analyzing finger- (Continued)

printing by GC-IMS, establishing a regression prediction model by performing a regression on a myofibrillar protein extraction ratio and a number of different types of volatile flavor substances, comparing characteristic regions acquired by the fingerprinting, conducting a principal component analysis (PCA), and determining, by the prediction model, a doneness degree and a flavor characteristic of a target sturgeon meat sample effectively.

7 Claims, 14 Drawing Sheets

(56) References Cited

FOREIGN PATENT DOCUMENTS

| CN | 107782814 A | * | 3/2018 | ............ G01N 30/02 |
|---|---|---|---|---|
| CN | 110100942 A | | 8/2019 | |
| CN | 110521963 A | | 12/2019 | |
| CN | 111929397 A | | 11/2020 | |
| CN | 112505169 A | | 3/2021 | |
| CN | 113189251 A | | 7/2021 | |

OTHER PUBLICATIONS

Yongxia Xu, et al., Effect of heat treatment on the binding of selected flavor compounds to myofibrillar proteins, Journal of the Science of Food and Agriculture, 2019, pp. 5028-5034, vol. 99.

* cited by examiner

METHOD FOR DETERMINING DEGREE OF DONENESS OF STURGEON MEAT BASED ON FLAVOR FINGERPRINTING AND PARTIAL LEAST SQUARES (PLS) REGRESSION

CROSS REFERENCES TO THE RELATED APPLICATIONS

The application is the national phase entry of International Application No. PCT/CN2022/081677, filed on Mar. 18, 2022, which is based on and claims priority on Chinese patent application No. 202110359191.0, filed on Apr. 1, 2021, the entire contents of which are incorporated herein by reference.

TECHNICAL FIELD

The present disclosure belongs to the technical field of flavor analysis and, in particular, relates to a method for determining a degree of doneness of sturgeon meat based on a flavor fingerprinting and a partial least squares (PLS) regression.

BACKGROUND

Common heat treatment techniques for sturgeon meat, include blanching, marinating, and pre-cooking or cooking sturgeon meat. The degree of doneness and flavor characteristic of sturgeon meat vary in different processing methods for different consumption patterns. Cooking kills all kinds of bacteria and pathogenic bacteria parasitic in fish, denatures proteins, and triggers fat oxidation, thereby giving fish products a unique flavor and taste. If the heating temperature is not high enough and the cooking time is not long enough, the interior of the fish will not be thoroughly cooked, which will affect the taste and lead to the risk of microbial infection. Conversely, over-cooking will lead to a loss of nutritional value and edibleness. Therefore, it is very important to determine the degree of doneness for the sturgeon meat processing industry.

At present, there is no simple and accurate method for determining the degree of doneness of sturgeon meat during heat treatment. Usually, it is determined by the myofibrillar protein extraction ratio. However, the determination of the myofibrillar protein extraction ratio is complex, time-consuming, and unstable due to human factors.

Flavor characteristics are the key factors for determining the edible quality of fish products, and they vary in fish with different degrees of doneness. Gas chromatography-mass spectrometry (GC-MS) is one of the most used methods for the separation and identification of volatile flavor substances. It can be used for qualitative and quantitative analysis of multi-component mixtures and is widely used in the research of the fermented flavor of wine, the flavor change of meat in processing, and the flavor detection of food freshness. Gas chromatography-ion mobility spectrometry (GC-IMS) is used to label and identify different gas-phase ions through their different mobility in the electric field. GC-IMS has the benefits of high separation performance of GC and high sensitivity of IMS and has the advantages of rapidity, accuracy, simplicity, and low cost. Taking sturgeon meat as an object, the present disclosure acquires the flavor components and fingerprints of heat-treated sturgeon meat through GC-MS and GC-IMS. The present disclosure further conducts linear fitting with the traditional index of myofibril extraction ratio to establish a doneness prediction model. The present disclosure is innovative in theory and technology and has practical value.

SUMMARY

To solve the problem of complicated and unstable operation in the existing method for determining the degree of doneness of sturgeon meat through the myofibril extraction ratio, an objective of the present disclosure is to propose a method for determining a degree of doneness of sturgeon meat based on flavor fingerprinting and a partial least squares (PLS) regression. The present disclosure determines the degree of doneness and flavor characteristic of the sturgeon meat through a regression analysis of a myofibrillar protein extraction ratio and contents of characteristic flavor substances, an analysis of characteristic regions of a flavor fingerprint by gas chromatography-ion mobility spectrometry (GC-IMS), and a principal component analysis (PCA).

The objective of the present disclosure is achieved by the following technical solution. A method for determining a degree of doneness of sturgeon meat based on flavor fingerprinting and PLS regression includes the following steps:

(1) shaping sturgeon meat to a fixed size and heating the sturgeon meat at different temperatures for different times;

(2) pulping the sturgeon meat heated in step (1); pipetting 11-15 mL of sturgeon meat pulp into a 20 mL headspace vial, sealing, and equilibrating the headspace vial at 50-52° C. for 25-30 min; inserting an extraction head into the headspace vial to allow adsorption at a distance of 1-2 cm from a liquid surface for 25-30 min; and inserting the extraction head into a GC injection port, desorbing at 235-245° C. for 2 min, and conducting a GC-MS analysis;

(3) loading 1-5 g of the sturgeon meat heated in step (1) into a 20 mL headspace vial, sealing, and incubating at 45-55° C. for 15-25 min; and taking, by a syringe at 80-90° C., 490-510 μL of headspace gas from the headspace vial for a GC-IMS analysis;

(4) measuring a myofibrillar protein content of the sturgeon meat heated in step (1) and calculating a myofibrillar protein extraction ratio, which is a ratio of a myofibrillar protein content of the sturgeon meat after heating to a myofibrillar protein content of the sturgeon meat before heating;

(5) establishing a multivariate linear fit curve by a PLS regression by taking the myofibrillar protein extraction ratio as a response variable and an amount of volatile flavor substances as independent variables, directly comparing characteristic regions of a fingerprint by GC-IMS, and conducting a PCA; and (6) determining a degree of doneness of a target sturgeon meat sample by acquiring GC-MS and GC-IMS data of the target sturgeon meat sample, analyzing through the multivariate linear fit curve established in step (5), and comparing characteristic regions of a fingerprint and conducting a PCA according to the step (5).

Further, step (1) may specifically include shaping raw sturgeon meat to 3 cm×3 cm×1 cm, and vacuum-heating at 50° C., 70° C., and 100° C. each for 15 min and 30 min, respectively.

Further, in the GC-MS analysis in step (2), a GC analysis may be conducted by a chromatographic column, which may feature splitless injection, an inlet temperature of 240° C., and a constant flow rate of 1 mL/min. The GC analysis may include temperature programming: holding 35° C. for 3 min, raising the temperature to 220° C. at 3° C./min, and holding for 10 min. An MS analysis may be conducted by a 230° C. electron impact (EI) ion source and 150° C. quadrupoles with a mass range of 33-500 amu.

Further, in the GC-IMS analysis in step (3), a GC analysis may be conducted by programming a flow rate of high-purity nitrogen (99%), which may serve as a carrier gas: holding an initial flow rate of 2 mL/min for 2 min, and raising the flow rate to 10 mL/min at 10 min, 100 mL/min at 20 min, and 150 mL/min at 30 min. An IMS analysis may be conducted by controlling a flow rate of a drift gas at 150 mL/min.

Further, in step (4), the myofibrillar protein content may be determined by using a Coomassie brilliant blue method. The myofibrillar protein extraction ratio may be calculated by $$A(\%) = \frac{P}{C} \times 100,$$

where A denotes the myofibrillar protein extraction ratio (%); P denotes the myofibrillar protein content of the sturgeon meat after heating (mg/100 g); and C denotes the myofibrillar protein content of the sturgeon meat before heating (mg/100 g).

Further, in step (5), the multivariate linear fit curve between the myofibrillar protein extraction ratio and information about different types of volatile flavor substances may be expressed by: $Y=16.8553+0.0496382X_1-0.0167546X_2+0.0284132X_3-0.0359706X_4+0.0106525X_5-0.0796625X_6-0.0192646X_7+0.0360119X_8+0.0194102X_9+0.0196761X_{10}$, where $X_1$, $X_2$, $X_3$, $X_4$, $X_5$, $X_6$, $X_7$, $X_8$, $X_9$, and $X_{10}$ denote the contents of 2-butanone monomer, ethyl acetate monomer, acetylacetone monomer, acetylacetone dimer, n-nonanal, octanoic acid, hexanal dimer, heptanal monomer, 1-hexanol monomer, and cyclohexanone, respectively.

Further, step (5) may specifically include: conducting a comparative analysis of the fingerprint by GC-IMS to acquire characteristic regions of the volatile flavor substances, which are used to characterize a flavor characteristic of the sturgeon meat, and conducting a dynamic PCA by a Dynamic PCA plug-in to cluster volatile flavor substances and quickly determine a type of an unknown volatile flavor substance.

Compared with the prior art, the present disclosure has the following beneficial effects:

The present disclosure acquires flavor components and fingerprints of heat-treated sturgeon meat through GC-MS and GC-IMS. The present disclosure conducts linear fitting with the traditional index of myofibril extraction ratio to establish a doneness prediction model. The present disclosure is innovative and practical. The present disclosure solves the problem of complicated and inaccurate operation in the traditional method for determining the degree of doneness of sturgeon meat through the myofibril extraction ratio. The present disclosure is simple in operation, short in detection time, high in detection efficiency, fast and effective, and can be widely used in the determination of the degree of doneness and flavor characteristics of other fish meat.

DETAILED DESCRIPTION OF THE EMBODIMENTS

Figure 1:
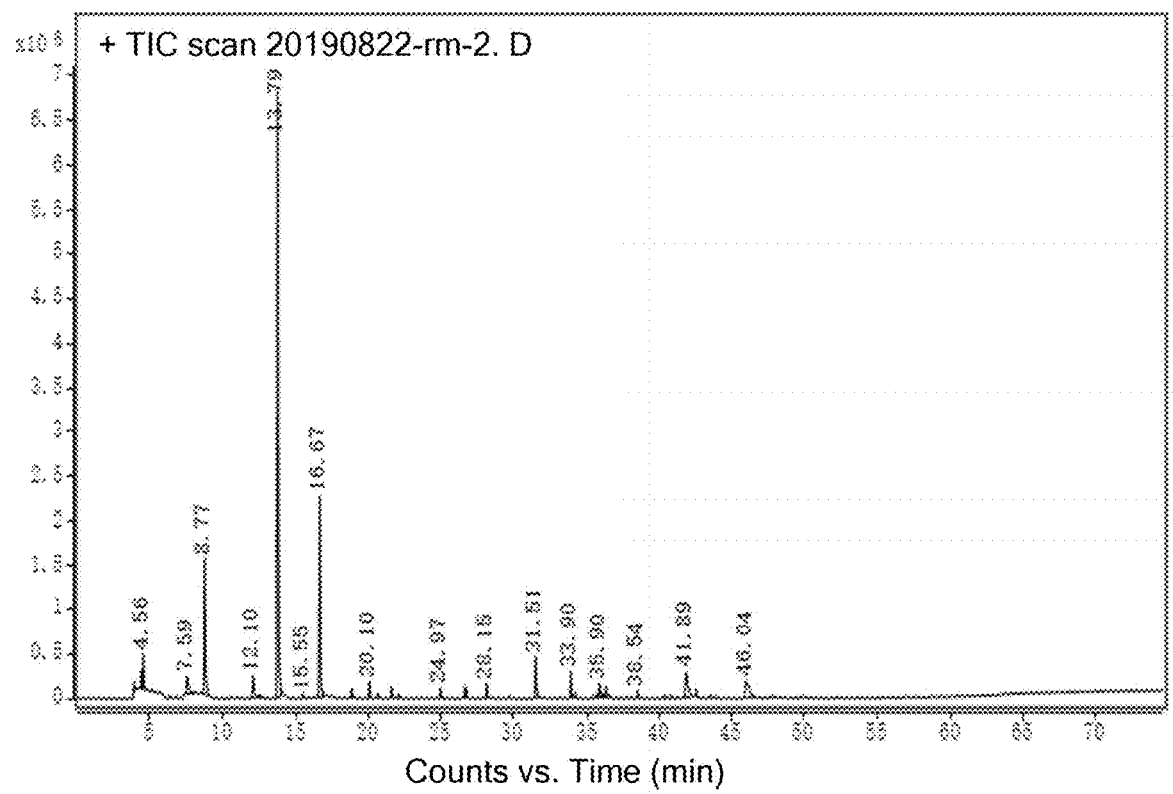
FIGS. 1 to 6 show total ion chromatograms (TICs) of flavor components of modeling standard sturgeon meat samples with different degrees of doneness according to the examples of the present disclosure.
Figure 2:
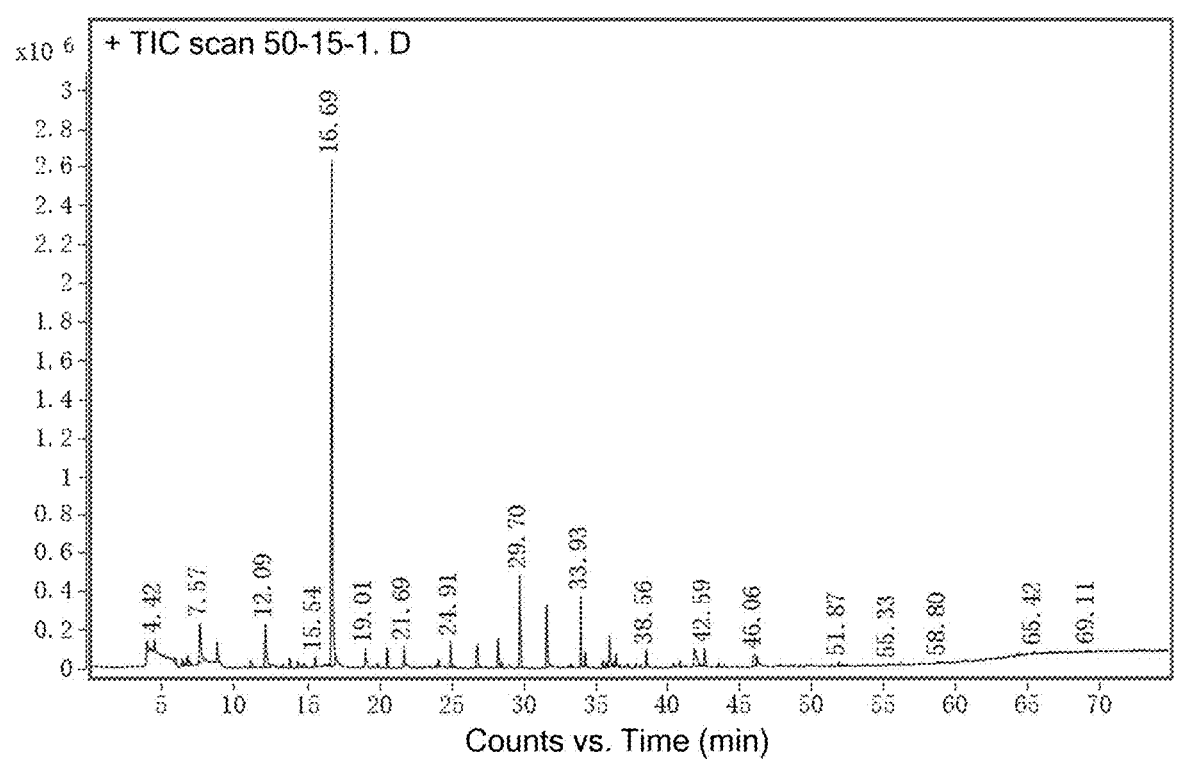
Figure 3:
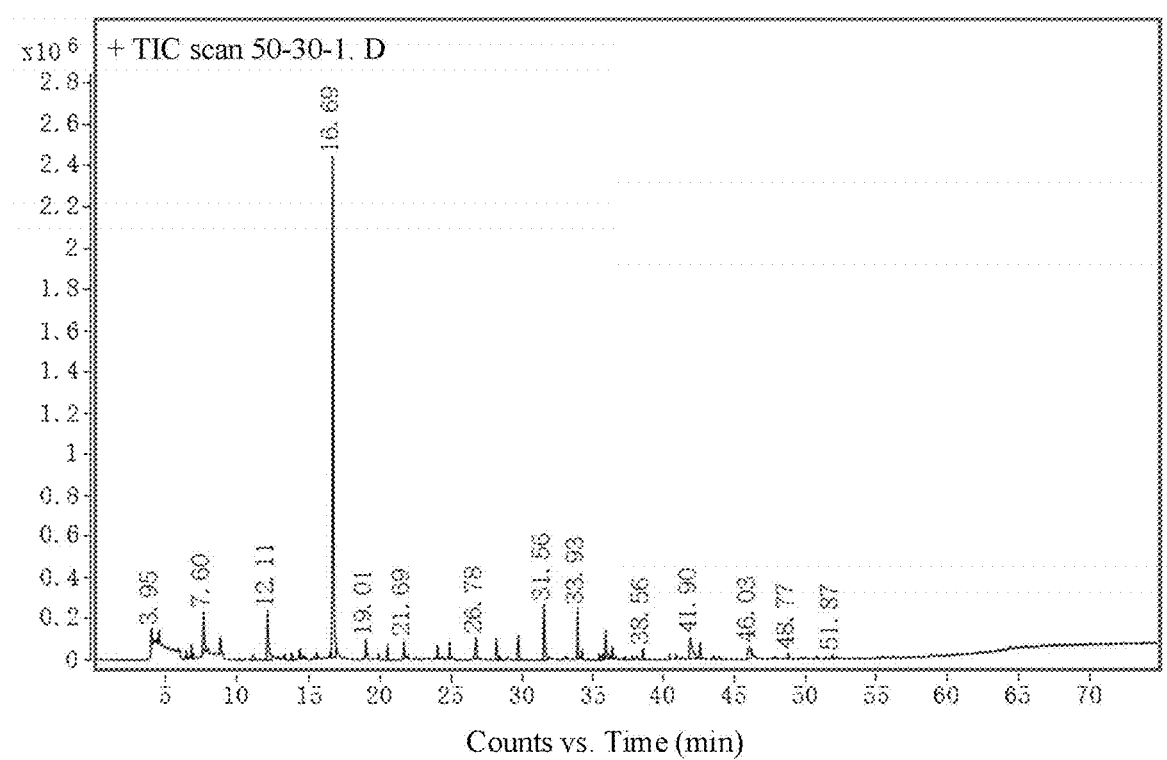
Figure 4:
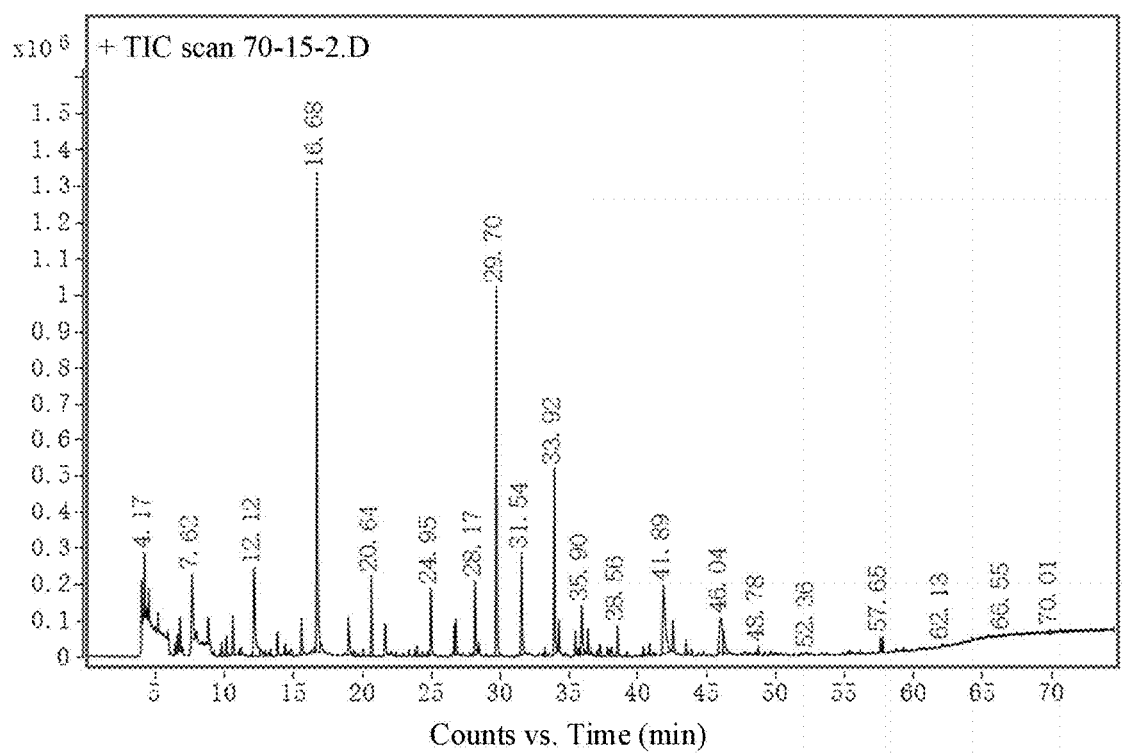
Figure 5:
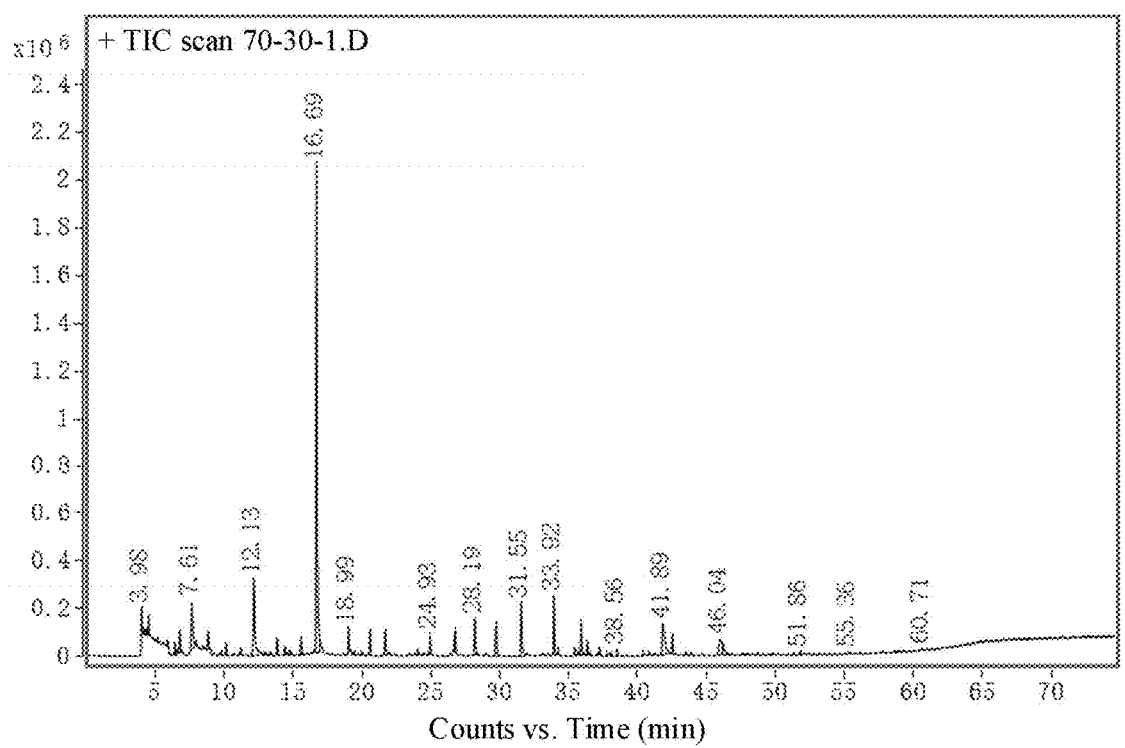
Figure 6:
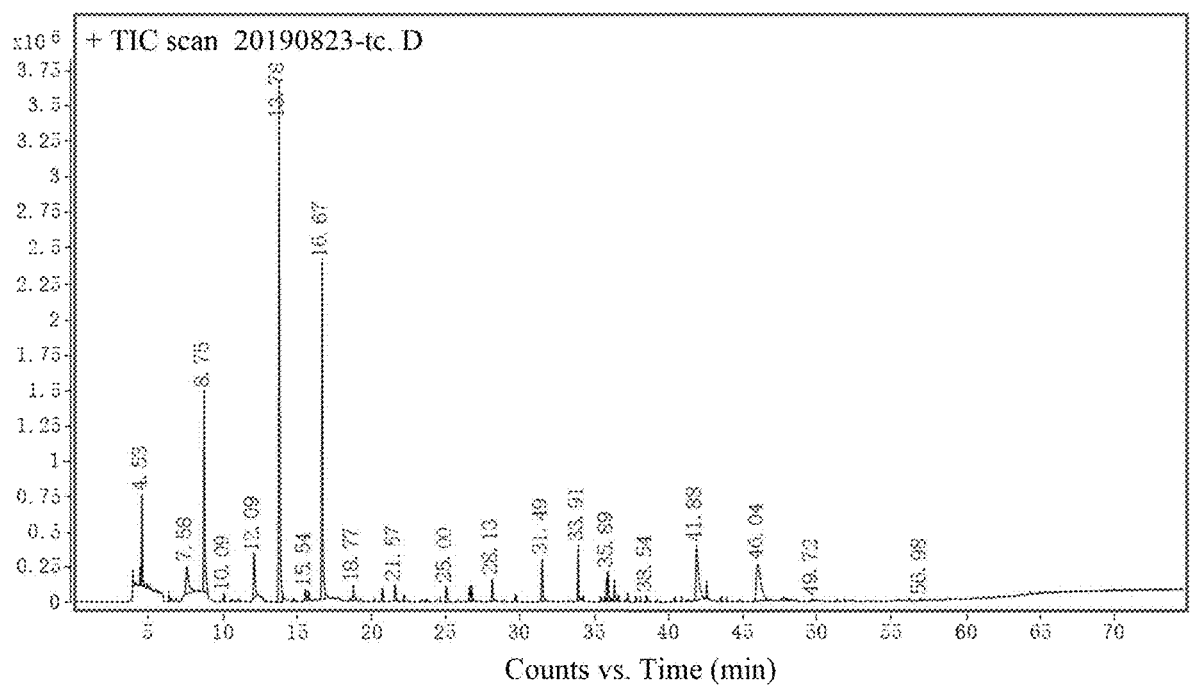

In order to make the objectives, technical solutions, and advantages of the present disclosure clearer, the implementations of the present disclosure will be further described in detail in conjunction with the drawings.

Example 1

The present disclosure provides a method for determining a degree of doneness of sturgeon meat based on flavor fingerprinting and a partial least squares (PLS) regression, which specifically includes the following steps:

(1) Sample Treatment

A frozen male Russian sturgeon was thawed for 0.5 h by flowing water, cut, and sampled along the spine. The cut sturgeon meat was shaped to 3 cm×3 cm×1 cm and washed through sterile water.

The temperatures of vacuum pans were respectively set at 50° C. (−880 bar), 70° C. (−700 bar), and 100° C. (1.01 bar), corresponding to a boiling point under vacuum. The sturgeon meat was completely immersed in water and heated for 15 min and 30 min, respectively. Then the sturgeon meat was removed from the vacuum pan and placed into a polyamide (PA)+cast polypropylene (CPP) bag for vacuum packaging. Raw meat samples were washed with sterile water and directly placed into PA+CPP bags for vacuum packaging, sequentially numbered as RAW, LTVH5015, LTVH5030, LTVH7015, LTVH7030, and TC10015.

(2) Gas Chromatography-Mass Spectrometry (GC-MS)

1) Extraction of Volatile Flavor Substances 10 g of the sturgeon meat was taken and pulped with 20 mL of distilled water. 13 mL of sturgeon meat pulp was pipetted into a 20 mL headspace vial, and the headspace vial was sealed with a cap (with a silicone septum). The headspace vial was equilibrated at 50° C. for 30 min. An extraction head was inserted into the headspace vial to allow adsorption at a distance of 1 cm from a liquid surface for 30 min. Then the extraction head was inserted into a GC injection port, and the desorption was conducted at 240° C. for 2 min for a GC-MS analysis.

2) GC-MS Analysis Conditions

The GC analysis was conducted by a chromatographic column, which featured splitless injection, a constant flow mode, an inlet temperature of 240° C., and a flow rate of 1 mL·min-1, and is subjected to temperature programming: hold 35° C. for 3 min, raise the temperature to 220° C. by 3° C.·min-1, and hold for 10 min. The MS analysis was conducted by a 230° C. electron impact (EI) ion source and 150° C. quadrupoles with a mass range of 33-500 amu.

3) Identification of Volatile Flavor Substances

The detected compounds were processed by MassHunter, and unknown substances were matched by NIST14 database. Only substances with forward and backward matching degrees greater than 750 were reported. Key flavor compounds were identified by a relative odor activity value (ROAV). That is, a component with the largest contribution to the flavor of the sample was defined as $ROAV_{stan}=100$, and other volatile components are calculated as follows:

$$ROAV_i \approx \frac{C_{ri}}{C_{rstan}} \times \frac{T_{stan}}{T_i} \times 100$$

$C_{ri}$: relative percentage of the volatile component;
$C_{rstan}$: relative percentage of the component with the largest contribution to the overall flavor of the sample;
$T_i$: sensory threshold of the volatile component;
$T_{stan}$: sensory threshold of the component with the largest contribution to the overall flavor of the sample.

(3) Determination of Myofibrillar Protein Content 15.00 g of the sample was weighed and added into 110 mL of buffer A (20 mmol/L phosphate buffer, including 100 mmol/L NaCl and 1 mmol/L EDTA, pH=7.0). The sample and the buffer were mixed well, homogenized at 15,000 r/min for 60 s, and centrifuged at 4° C. at 8,000 r/min for 10 min. Then the supernatant was removed. 50 mL of buffer A was added to a precipitate, and homogenization was conducted for 60 s. Centrifugation was conducted again under the same conditions to yield a precipitate. This operation was repeated twice. 30 mL of buffer B (25 mmol/L phosphate buffer, including 0.6 mol/L NaCl, pH=7.0) was added to the final precipitate, and homogenization was conducted. Then the mixture was placed in a 4° C. refrigerator overnight to dissolve. Centrifugation was conducted at 4° C. at 10,000 r/min for 10 min, and an insoluble fraction was removed to acquire a supernatant, namely a myofibrillar protein solution. Using bovine serum albumin as a standard curve, the concentration of the solution was determined by a Coomassie brilliant blue method.

(4) Gas Chromatography-Ion Mobility Spectrometry (GC-IMS)

2 g of the mixed sample was weighed, placed into a 20 mL headspace vial, and incubated at 50° C. for 20 min. 500 µL of the sample was injected via an 85° C. syringe. Analytical detection was conducted by a GC-IMS flavor analyzer, and each sample was replicated 3 times. The GC was conducted in the conditions shown in the table below:

TABLE 1

| GC conditions of Example 1 | | | |
|---|---|---|---|
| Time | E1 | E2 | R |
| 00:00,000 | 150 mL/min | 2 ml/min | Rec |
| 02:00,000 | 150 mL/min | 2 ml/min | — |
| 10:00,000 | 150 mL/min | 10 ml/min | — |
| 20:00,000 | 150 mL/min | 100 ml/min | — |
| 30:00,000 | 150 mL/min | 150 ml/min | Stop |

GC-IMS data processing and analysis: The analysis software includes Laboratory Analytical Viewer (LAV), three plug-ins, and GC×IMS Library Search, which can analyze the samples from different angles. LAV is configured to view the analytical spectrum, where each point in the graph represents a volatile organic compound, and can be quantitatively analyzed by establishing a standard curve. The Reporter plug-in is configured to directly compare spectral differences between the samples. The Gallery Plot plug-in (Fingerprint Comparison) is configured to visually and quantitatively compare differences in the volatile organic compounds between different samples. The Dynamic PCA plug-in is configured to cluster substances and quickly determine the type of unknown substances. GC×IMS Library Search is the built-in NIST database and IMS database of the application software, which can conduct a qualitative analysis of substances.

Figure 7:
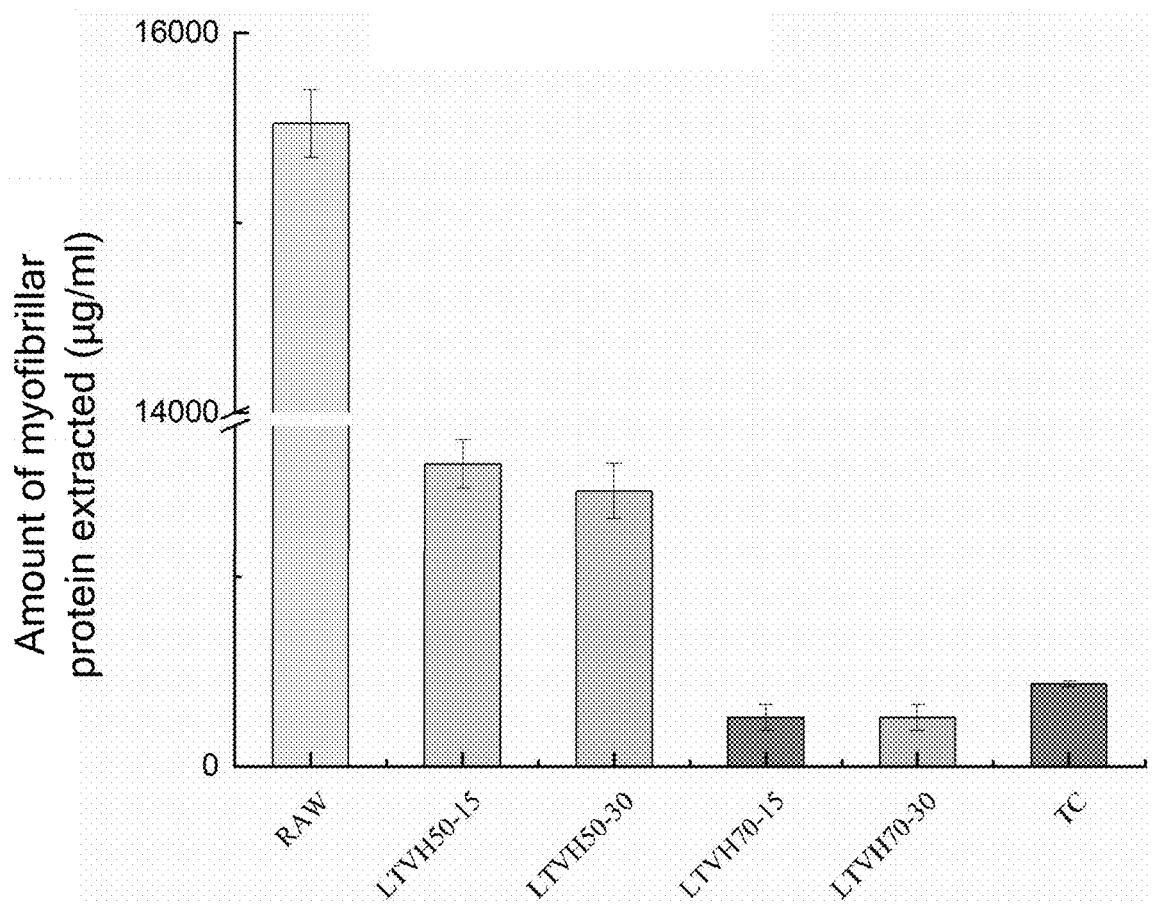
FIG. 7 shows myofibrillar protein contents of the modeling standard sturgeon meat samples with different degrees of doneness according to the examples of the present disclosure.
Figure 8:
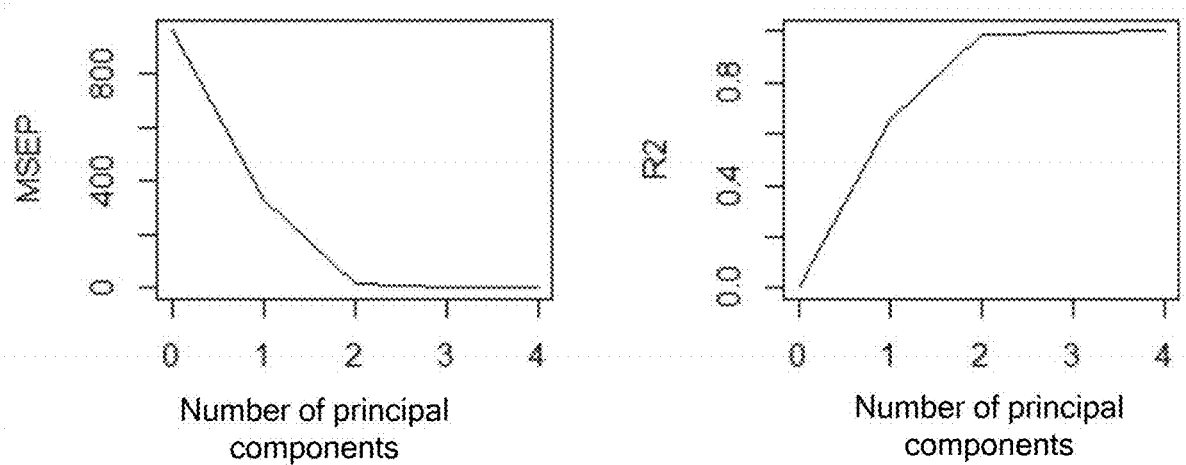
FIG. 8 shows a mean squared error of prediction (MSEP) and $R^2$ as a function of a number of principal components according to an example of the present disclosure.
Figure 9:
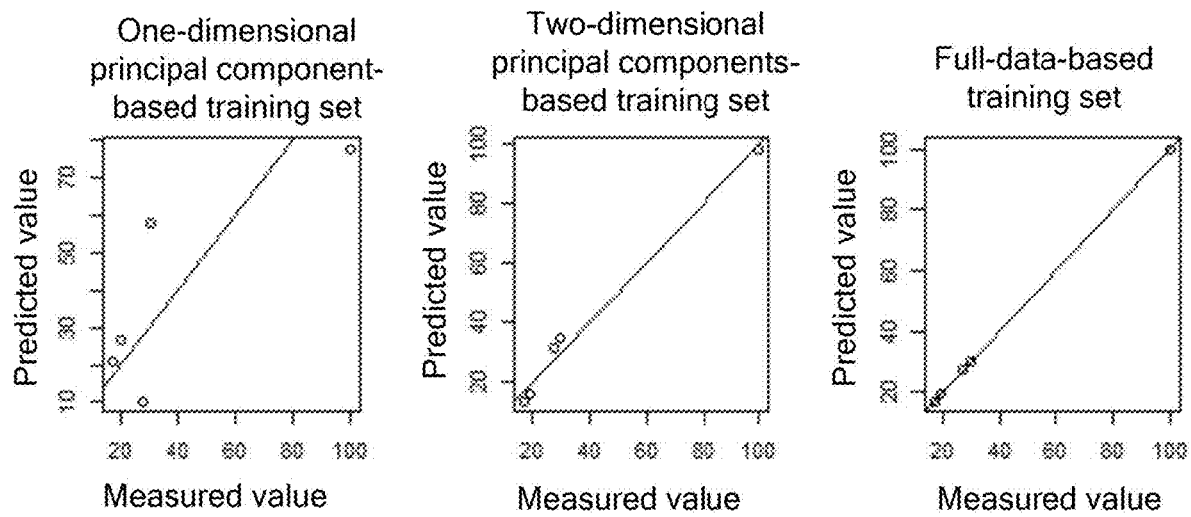
FIG. 9 shows a regression of a training set of principal components of different dimensions according to an example of the present disclosure.
Figure 10:
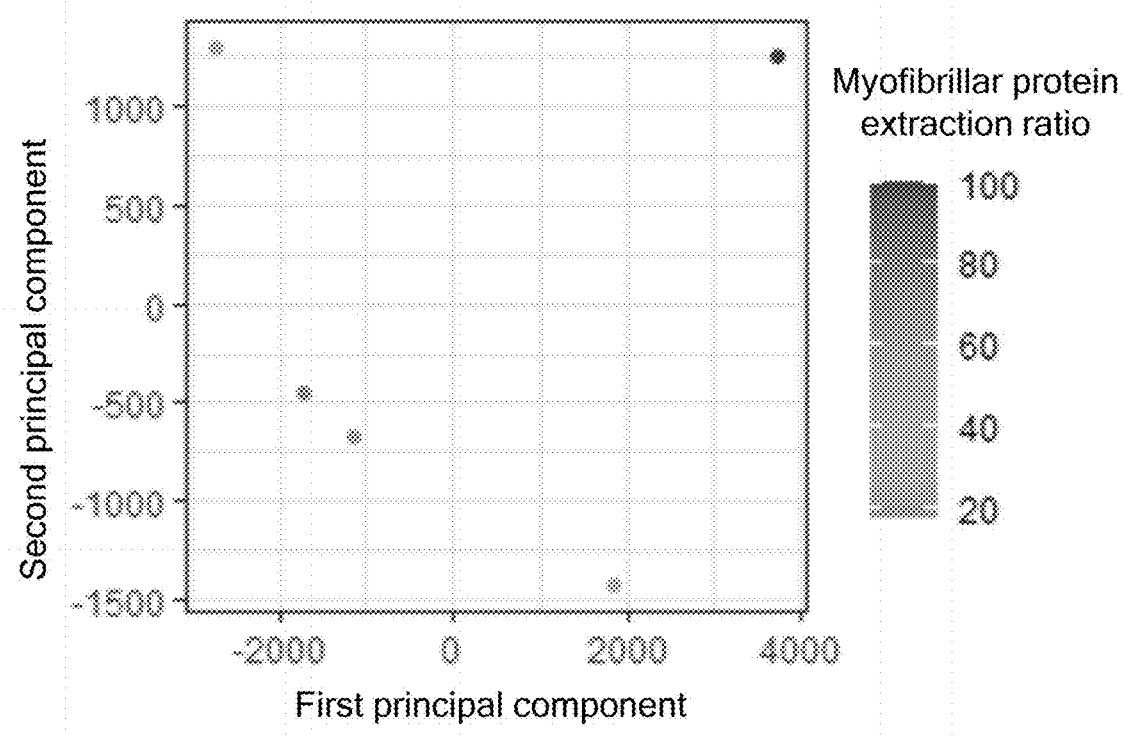
FIG. 10 shows a score for a myofibrillar protein extraction ratio according to an example of the present disclosure.
Figure 11:
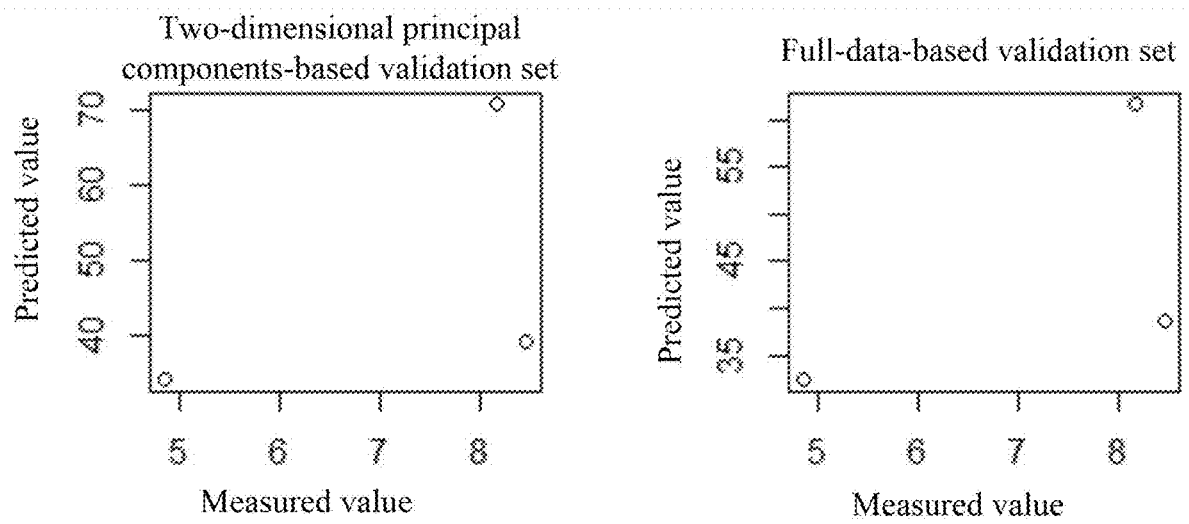
FIG. 11 shows a validation regression of a prediction model according to an example of the present disclosure.

(5) Establishment of a Regression Prediction Equation for Flavor Components of Modeling Standard Sturgeon Meat FIGS. 1 to 6 show total ion chromatograms (TICs) of modeling standard sturgeon meat samples with different degrees of doneness. The myofibrillar protein content was determined by the Coomassie brilliant blue method, and the changes in the myofibrillar protein extraction ratio of the modeling standard sturgeon meat samples with different degrees of doneness are shown in FIG. 7. Partial least squares (PLS) regression analysis was conducted by using RAW, LTVH50-15, LTVH50-30, LTVH70-15, LTVH70-30 and TC100-15 as training sets and LTVH60-15 and LTVH60-30 as validation sets. As shown in FIG. 8, when the number of principal components was 2, the mean squared error of prediction (MSEP) decreased significantly and then remained basically unchanged, and the R2 increased significantly and then remained basically unchanged. Therefore, the number of principal components for dimensionality reduction was determined to be 2. The model training results are shown in FIG. 9. The prediction accuracy of the PLS model using the first two components was almost the same as that of the full model, and the first two components were sufficient to represent the overall characteristics of the dataset. According to the score plot (FIG. 10), the myofibrillar protein extraction ratio had an increasing trend along the first and second principal components. It was further tested whether the model had desired predictive performance through the validation set. As shown in FIG. 11, for the test set data, the prediction effect of the constructed PLS regression model was still desired. After analyzing the contribution of all independent variables, 10 factors with the highest weight ratio were screened out, and their regression coefficients were calculated. Thus, the regression curve between the myofibrillar protein extraction ratio and a number of different types of volatile flavor substances was expressed by: $Y=16.8553+0.0496382X_1-0.0167546X_2+0.0284132X_3-0.0359706X_4+0.0106525X_5-0.0796625X_6-0.0192646X_7+0.0360119X_8+0.0194102X_9+0.0196761X_{10}$, where $X_1, X_2, X_3, X_4, X_5, X_6, X_7, X_8, X_9$, and $X_{10}$ denoted the contents of 2-butanone monomer, ethyl acetate monomer, acetylacetone monomer, acetylacetone dimer, n-nonanal, octanoic acid, hexamethylene dimer, heptanal monomer, 1-hexanol monomer, and cyclohexanone, respectively. Through this expression, the myofibrillar protein extraction ratio could be inferred from the content of each flavor component to determine the degree of doneness of the sturgeon meat.

(6) Fingerprinting on Flavor Components of Modeling Standard Sturgeon Meat

Figure 12:
FIG. 12 shows a fingerprint of flavor components of modeling standard sturgeon meat samples with different degrees of doneness according to an example of the present disclosure.

According to FIG. 12, the flavor substances of the sturgeon meat gradually changed with the increase of the degree of doneness. In general, the contents of the volatile flavor substances in the sturgeon meat gradually increased and then decreased. Region 2 was a relatively concentrated region of aldehydes. In this region, nonanal, benzaldehyde, and heptanal did not change much in each treatment group, while octanal, hexanal, and pentanal first increased and then decreased. Regions 1 and 4 were concentrated by 2-pentanone, 3-octanol, and 1-hexanol, showing a trend of first increasing and then decreasing. In a left-to-right direction, Region 3 was occupied from left to right by acetone, 2-butanone, 3-methylbutyraldehyde, and acetoin, which all increased gradually. Therefore, the doneness of the sturgeon meat could be determined based on the contents of the volatile flavor substances in Region 3.

(7) PCA on Flavor Components of Modeling Standard Sturgeon Meat

Figure 13:
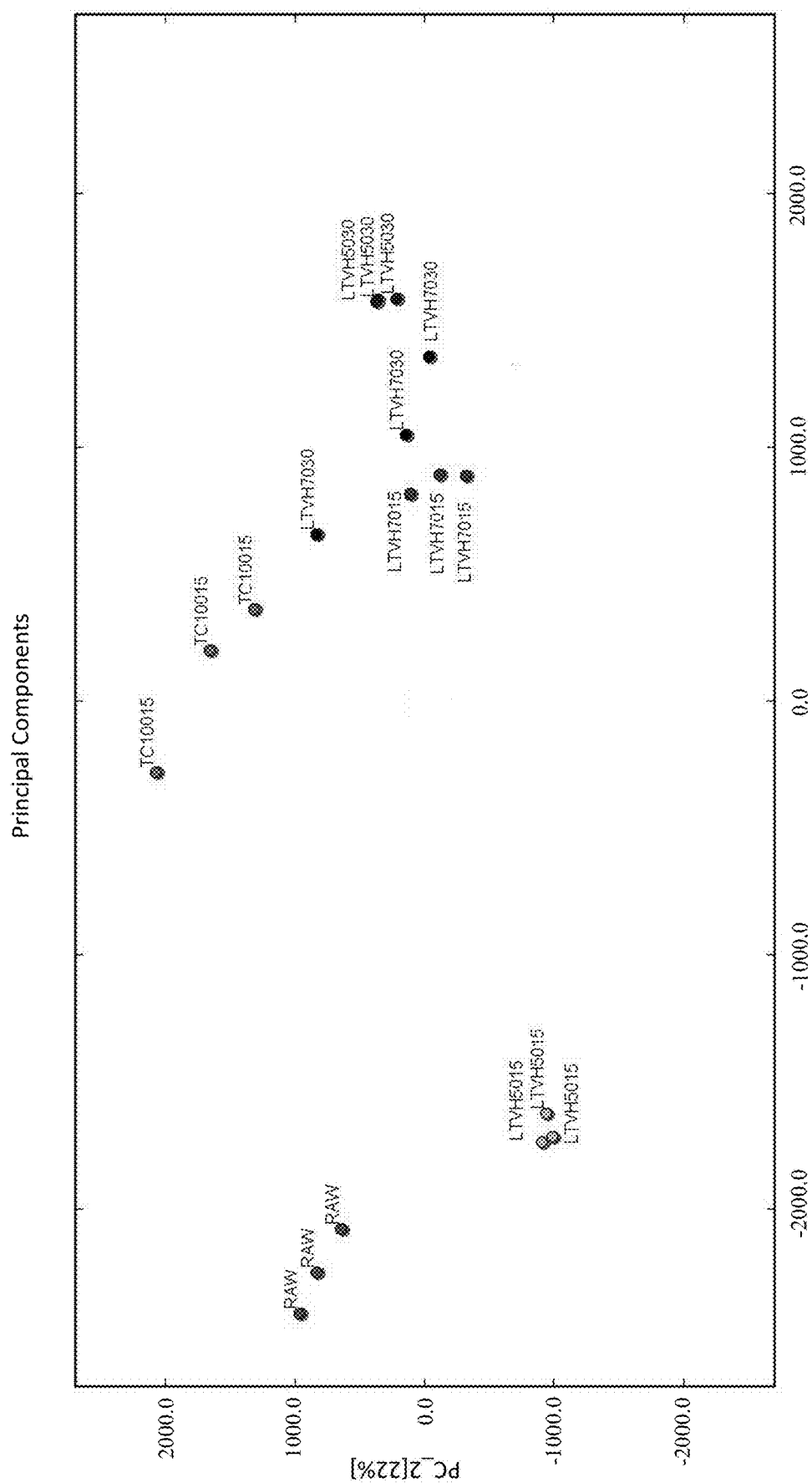
FIG. 13 shows a principal component analysis (PCA) plot of the flavor components of the modeling standard sturgeon meat samples with different degrees of doneness according to the example of the present disclosure.

According to FIG. 13, the contribution rates of the first principal component axis and the second principal component axis were 35% and 27%, respectively, and the total contribution rate was 62%. This indicates that the principal components could better reflect most of the characteristic information of the volatile flavor substances in the sturgeon meat with different degrees of doneness. The differences between the sturgeon meat samples in different treatment groups are clearly demonstrated in the figure. The sturgeon meat samples close to each other indicated a small difference in the components, and those far apart indicated an obvious difference in the components. With the increase in the degree of doneness, the sturgeon samples showed a regular distribution from the bottom left to the upper right, indicating that the PCA could well distinguish the sturgeon meat with different degrees of doneness.

(8) Determination and Analysis of Samples to be Tested

In this example, the sturgeon meat treated at 60° C. for 15 min was used as the test object, and the GC-MS test method is the same as the above method and will not be repeated herein.

Figure 14A:
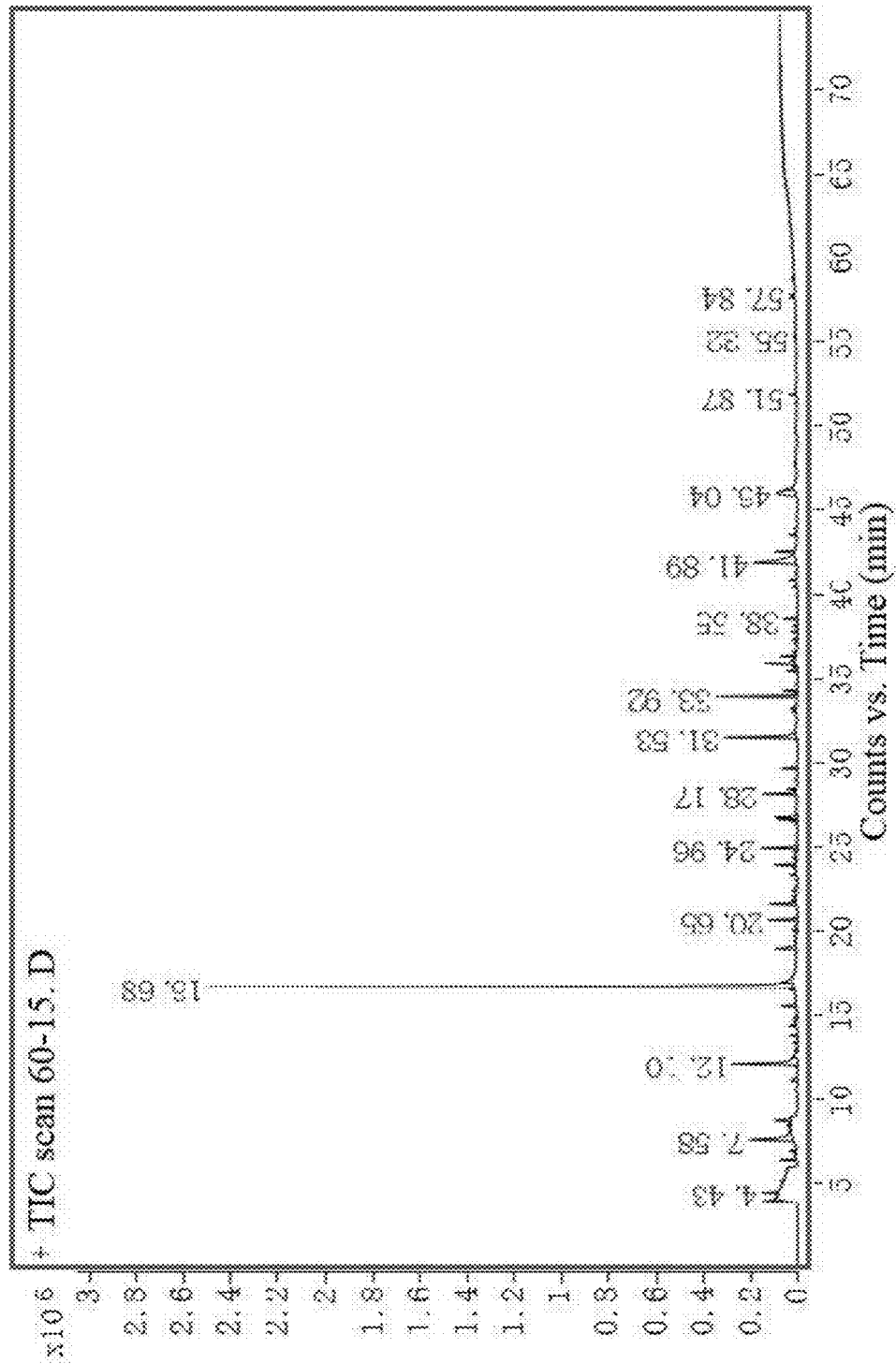
FIGS. 14A and 14B show a TIC of flavor components of a target sturgeon meat sample according to an example of the present disclosure.

The TIC of the sample to be tested is shown in FIG. 14A. According to the prediction of the regression curve between the myofibrillar protein extraction ratio and the number of different types of volatile flavor substances, the types and contents of the volatile flavor substances in LTVH60-15 are shown in Table 2. The myofibrillar protein content calculated by the prediction model was 19.47655%, and the actual myofibrillar protein content was 19.47652% with a relative deviation of prediction being 0.00020%. This shows that the regression curve could well predict the myofibrillar protein extraction ratio of the sample to determine the degree of doneness.

TABLE 2

Types and peak volumes of volatile flavor substances in the sample in Example 1

| | LTVH50-15 | LTVH50-30 | LTVH60-15 | LTVH70-15 | LTVH70-30 | TC100-15 |
|---|---|---|---|---|---|---|
| Acetone | 1092.515 | 3166.211333 | 1520.753667 | 2301.943667 | 2713.151 | 3875.865667 |
| 2-butanone monomer | 833.609 | 1451.395 | 804.9213333 | 1040.750333 | 1099.156333 | 1282.438333 |
| Ethyl acetate monomer | 635.4893333 | 539.739 | 525.6893333 | 402.8853333 | 492.49 | 414.754 |
| Ethyl acetate dimer | 188.5713333 | 142.6596667 | 143.4473333 | 76.10566667 | 120.1766667 | 118.434 |
| 3-methylbutanal monomer | 555.6446667 | 558.217 | 265.655 | 262.0243333 | 388.5626667 | 711.0326667 |
| 3-methylbutanal dimer | 254.9526667 | 158.7236667 | 60.83766667 | 53.41633333 | 96.98366667 | 371.9613333 |
| Acetylacetone monomer | 1316.502667 | 534.3076667 | 977.4813333 | 1484.413333 | 1096.660667 | 1881.913667 |
| Acetyl dimer | 315.3886667 | 258.7856667 | 228.4673333 | 441.6536667 | 331.826 | 721.338 |
| Benzaldehyde | 156.3466667 | 274.7236667 | 152.481 | 149.5026667 | 167.2806667 | 151.2143333 |
| N-nonanal | 364.0623333 | 315.044 | 297.1036667 | 371.7013333 | 323.7786667 | 301.0543333 |
| Octanoic acid | 172.8633333 | 396.942 | 222.5953333 | 372.3293333 | 350.9216667 | 285.3846667 |
| Pentanal monomer | 430.192 | 1015.541 | 809.396 | 727.9783333 | 879.769 | 383.2993333 |
| Hexanal monomer | 1462.463333 | 2796.367667 | 2614.102333 | 2628.669333 | 2710.688333 | 2080.02 |
| Hexanal dimer | 829.22 | 5501.522 | 4014.124667 | 3197.962667 | 3930.321333 | 1767.170667 |
| Heptanal dimer | 59.59 | 220.8683333 | 75.939 | 98.40366667 | 107.1266667 | 64.89066667 |

TABLE 2-continued

Types and peak volumes of volatile flavor substances in the sample in Example 1

|  | LTVH50-15 | LTVH50-30 | LTVH60-15 | LTVH70-15 | LTVH70-30 | TC100-15 |
|---|---|---|---|---|---|---|
| 1-hexanol dimer | 43.097 | 43.744 | 54.921 | 191.5953333 | 200.226 | 216.6623333 |
| Heptanal monomer | 417.7313333 | 1076.712 | 616.307 | 862.984 | 874.0033333 | 655.828 |
| 1-hexanol monomer | 73.35133333 | 99.75533333 | 253.6173333 | 683.6673333 | 684.4076667 | 705.0966667 |
| 3-octanol | 65.024 | 193.4856667 | 128.9926667 | 180.3263333 | 206.214 | 131.8523333 |
| 2-butanone dimer | 64.77933333 | 1087.649 | 119.427 | 415.128 | 652.547 | 1108.438333 |
| 2-heptanone | 46.48566667 | 89.10033333 | 63.10266667 | 87.34566667 | 78.67833333 | 74.84433333 |
| Pentanal dimer | 32.607 | 588.2113333 | 151.7076667 | 124.424 | 243.453 | 53.91366667 |
| 2-pentanone monomer | 63.09333333 | 35.60466667 | 55.17166667 | 79.578 | 59.499 | 77.68733333 |
| 2-pentanone dimer | 25.54 | 160.3286667 | 45.65866667 | 76.48933333 | 70.797 | 72.98033333 |
| Cyclohexanone | 35.36466667 | 195.4366667 | 49.95233333 | 58.00633333 | 69.797 | 48.689 |
| Predicted myofibrillar protein extraction ratio (%) | 29.99896 | 27.32501 | 19.47651 | 8.463198 | 4.850957 | 8.159824 |
| Actual myofibrillar protein extraction ratio (%) | 29.99899 | 27.32503 | 19.47655 | 8.463249 | 4.851009 | 8.159876 |
| Relative deviation of prediction (%) | 0.000122247 | 9.66431E−05 | 0.000199197 | 0.000606532 | 0.001063612 | 0.000639678 |

(9) Verification of Prediction Results

Figure 15A:
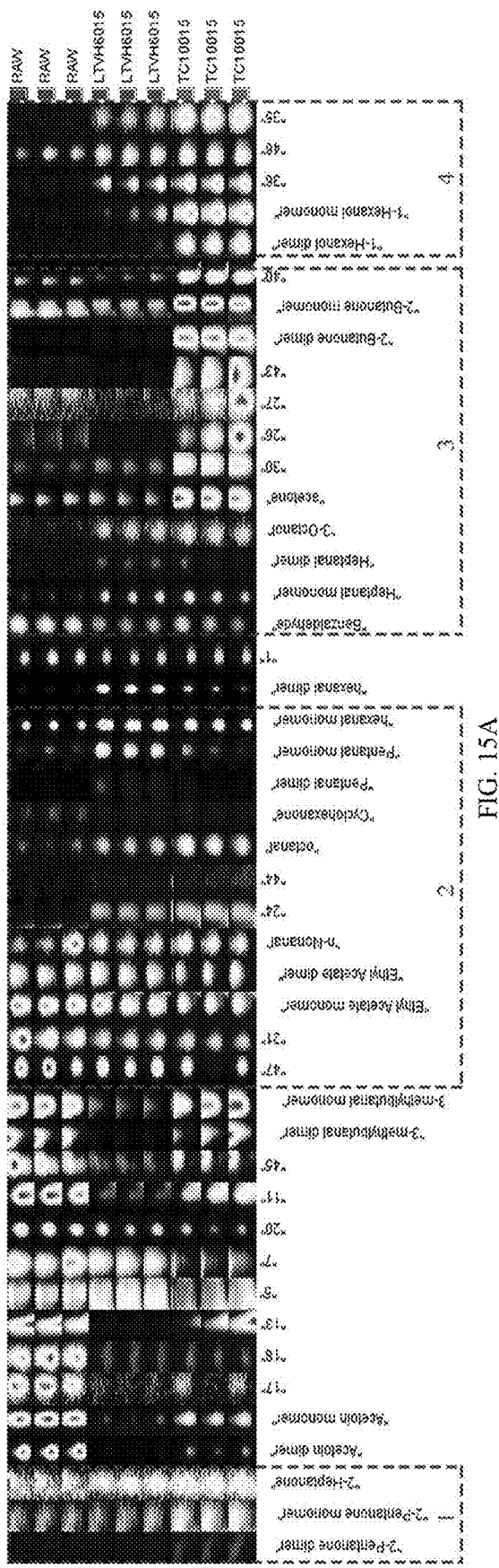
FIGS. 15A and 15B show a fingerprint of the flavor components of the target sturgeon meat sample according to an example of the present disclosure.

According to FIG. 15A, the fingerprints of the sturgeon meat treated at 60° C. for 15 min and other treatment groups were significantly different. In general, the types of the volatile flavor substances were significantly less than those of other treatment groups, and the amount of other flavor substances were lower except for the ethyl acetate in Region 2. This shows that GC-IMS could effectively distinguish the characteristic flavors of different samples to determine their degree of doneness.

Example 2

The present disclosure provides a method for determining a degree of doneness of sturgeon meat based on flavor fingerprinting and a partial least squares (PLS) regression, which specifically includes the following steps:

(1) Sample Treatment

A frozen male Russian sturgeon was thawed for 0.5 h by flowing water and was cut and sampled along the spine. The cut sturgeon meat was shaped to 3 cm×3 cm×1 cm and washed with sterile water.

The temperatures of vacuum pans were respectively set at 50° C. (−880 bar), 70° C. (−700 bar), 100° C. (1.01 bar), corresponding to a boiling point under vacuum. The sturgeon meat was completely immersed in water and was heated for 15 min and 30 min, respectively. Then the sturgeon meat was removed from the vacuum pan and placed into a polyamide (PA)+cast polypropylene (CPP) bag for vacuum packaging. Raw meat samples were washed with sterile water and directly placed into PA+CPP bags for vacuum packaging, sequentially numbered as RAW, LTVH5015, LTVH5030, LTVH7015, LTVH7030, and TC10015.

(2) Gas Chromatography-Mass Spectrometry (GC-MS)

1) Extraction of Volatile Flavor Substances 10 g of the sturgeon meat was weighed and pulped with 20 mL of distilled water. 13 mL of sturgeon meat pulp was pipetted into a 20 mL headspace vial, and the headspace vial was sealed with a cap (with a silicone septum). The headspace vial was equilibrated at 50° C. for 30 min. An extraction head was inserted into the headspace vial to allow adsorption at a distance of 1 cm from a liquid surface for 30 min. Then the extraction head was inserted into a GC injection port, and the desorption was conducted at 240° C. for 2 min for a GC-MS analysis.

2) GC-MS Analysis Conditions

The GC analysis was conducted by a chromatographic column, which featured splitless injection, a constant flow mode, an inlet temperature of 240° C., and a flow rate of 1 mL·min$^{-1}$, and is subjected to temperature programming: hold 35° C. for 3 min, raise the temperature to 220° C. by 3° C.·min$^{-1}$, and hold for 10 min. The MS analysis was conducted by a 230° C. electron impact (EI) ion source and 150° C. quadrupoles with a mass range of 33-500 amu.

3) Identification of Volatile Flavor Substances

The detected compounds were processed by MassHunter, and unknown substances were matched by NIST14 database. Only substances with forward and backward matching degrees greater than 750 were reported. Key flavor compounds were identified by a relative odor activity value (ROAV). That is, a component with the largest contribution to the flavor of the sample was defined as $ROAV_{stan}=100$, and other volatile components are calculated as follows:

$$ROAV_i \approx \frac{C_{ri}}{C_{rstan}} \times \frac{T_{stan}}{T_i} \times 100$$

$C_{ri}$: relative percentage of the volatile component;
$C_{rstan}$: relative percentage of the component with the largest contribution to the overall flavor of the sample;
$T_i$: sensory threshold of the volatile component; and
$T_{stan}$: sensory threshold of the component with the largest contribution to the overall flavor of the sample.

(3) Determination of Myofibrillar Protein Content 15.00 g of the sample was weighed and added into 110 mL of buffer A (20 mmol/L phosphate buffer, including 100 mmol/L NaCl and 1 mmol/L EDTA, pH=7.0). The sample and the buffer were mixed well, homogenized at 15,000 r/min for 60 s, and centrifuged at 4° C. at 8,000 r/min for 10 min. Then the supernatant was removed. 50 mL of buffer A was added to a precipitate, and homogenization was conducted for 60 s. Centrifugation was conducted again under the same conditions to yield a precipitate. This operation was repeated twice. 30 mL of buffer B (25 mmol/L phosphate buffer, including 0.6 mol/L NaCl, pH=7.0) was added to the final precipitate, and homogenization was conducted. Then the mixture was placed in a 4° C. refrigerator overnight to dissolve. Centrifugation was conducted at 4° C. at 10,000 r/min for 10 min, and an insoluble fraction was removed to acquire a supernatant, namely a myofibrillar protein solution. Using bovine serum albumin as a standard curve, the concentration of the solution was determined by a Coomassie brilliant blue method.

(4) Gas Chromatography-Ion Mobility Spectrometry (GC-IMS)

2 g of the mixed sample was weighed, placed into a 20 mL headspace vial, and incubated at 50° C. for 20 min. 500 µL of the sample was injected via an 85° C. syringe. Analytical detection was conducted by a GC-IMS flavor analyzer, and each sample was replicated 3 times. The GC was conducted in the conditions shown in the table below:

TABLE 3

GC conditions of Example 2

| Time | E1 | E2 | R |
| --- | --- | --- | --- |
| 00:00,000 | 150 mL/min | 2 ml/min | Rec |
| 02:00,000 | 150 mL/min | 2 ml/min | — |
| 10:00,000 | 150 mL/min | 10 ml/min | — |
| 20:00,000 | 150 mL/min | 100 ml/min | — |
| 30:00,000 | 150 mL/min | 150 ml/min | Stop |

GC-IMS data processing and analysis: The analysis software includes Laboratory Analytical Viewer (LAV), three plug-ins and GC×IMS Library Search, which can analyze the samples from different angles. LAV is configured to view the analytical spectrum, where each point in the graph represents a volatile organic compound, and can be quantitatively analyzed by establishing a standard curve. The Reporter plug-in is configured to directly compare spectral differences between the samples. The Gallery Plot plug-in (Fingerprint Comparison) is configured to visually and quantitatively compare differences in the volatile organic compounds between different samples. The Dynamic PCA plug-in is configured to cluster substances and quickly determine the type of unknown substances. GC×IMS Library Search is the built-in NIST database and IMS database of the application software, which can conduct a qualitative analysis of substances.

(5) Establishment of Regression Prediction Equation for Flavor Components of Modeling Standard Sturgeon Meat FIGS. 1 to 6 show the TICs of modeling standard sturgeon meat samples with different degrees of doneness. The myofibrillar protein content was determined by the Coomassie brilliant blue method, and the changes in the myofibrillar protein extraction ratio of the modeling standard sturgeon meat samples with different degrees of doneness are shown in FIG. 7. Partial least squares (PLS) regression analysis was conducted by using RAW, LTVH50-15, LTVH50-30, LTVH70-15, LTVH70-30 and TC100-15 as training sets and LTVH60-15 and LTVH60-30 as validation sets. As shown in FIG. 8, when the number of principal components was 2, the mean squared error of prediction (MSEP) decreased significantly and then remained basically unchanged, and the R2 increased significantly and then remained basically unchanged. Therefore, the number of principal components for dimensionality reduction was determined to be 2. The model training results are shown in FIG. 9. The prediction accuracy of the PLS model using the first two components was almost the same as that of the full model, and the first two components were sufficient to represent the overall characteristics of the dataset. According to the score plot (FIG. 10), the myofibrillar protein extraction ratio had an increasing trend along the first and second principal components. It was further tested whether the model had desired predictive performance through the validation set. As shown in FIG. 11, for the test set data, the prediction effect of the constructed PLS regression model was still desired. After analyzing the contribution of all independent variables, 10 factors with the highest weight ratio were screened out, and their regression coefficients were calculated. Thus, the regression curve between the myofibrillar protein extraction ratio and the number of different types of volatile flavor substances was expressed by: $Y=16.8553+0.0496382X_1-0.0167546X_2+0.0284132X_3-0.0359706X_4+0.0106525X_5-0.0796625X_6-0.0192646X_7+0.0360119X_8+0.0194102X_9+0.0196761X_{10}$, where $X_1$, $X_2$, $X_3$, $X_4$, $X_5$, $X_6$, $X_7$, $X_8$, $X_9$, and $X_{10}$ denoted the contents of 2-butanone monomer, ethyl acetate monomer, acetylacetone monomer, acetylacetone dimer, n-nonanal, octanoic acid, hexamethylene dimer, heptanal monomer, 1-hexanol monomer, and cyclohexanone, respectively. Through this expression, the myofibrillar protein extraction ratio could be inferred from the content of each flavor component to determine the degree of doneness of the sturgeon meat.

(6) Fingerprinting on Flavor Components of Modeling Standard Sturgeon Meat

According to FIG. 12, the flavor substances of the sturgeon meat gradually changed with the increase of the degree of doneness. In general, the contents of the volatile flavor substances in the sturgeon meat gradually increased and then decreased. Region 2 was a relatively concentrated region of aldehydes. In this region, nonanal, benzaldehyde, and heptanal did not change much in each treatment group, while octanal, hexanal, and pentanal first increased and then decreased. Regions 1 and 4 were occupied by 2-pentanone, 3-octanol, and 1-hexanol, showing a trend of increasing first and then decreasing. In a left-to-right direction, Region 3 was occupied from left to right by acetone, 2-butanone, 3-methylbutyraldehyde, and acetoin, which all increased gradually. Therefore, the doneness of the sturgeon meat could be determined based on the amount of the volatile flavor substances in Region 3.

(7) PCA on Flavor Components of Modeling Standard Sturgeon Meat

According to FIG. 13, the contribution rates of the first principal component axis and the second principal component axis were 35% and 27%, respectively, and the total contribution rate was 62%. This indicates that the principal components could better reflect most of the characteristic information of the volatile flavor substances in the sturgeon meat with different degrees of doneness. The differences between the sturgeon meat samples in different treatment groups are clearly demonstrated in the figure. The sturgeon meat samples that cluster close to each other indicated a small difference in the components, and those far apart indicated an obvious difference in the components. With the increase in the degree of doneness, the sturgeon samples showed a regular distribution from the bottom left to the upper right, indicating that the PCA could well distinguish the sturgeon meat with different degrees of doneness.

(8) Determination and Analysis of Samples to be Tested

In this example, the sturgeon meat treated at 60° C. for 30 min was used as the test object, and the GC-MS test method is the same as the above method and will not be repeated herein.

Figure 14B:
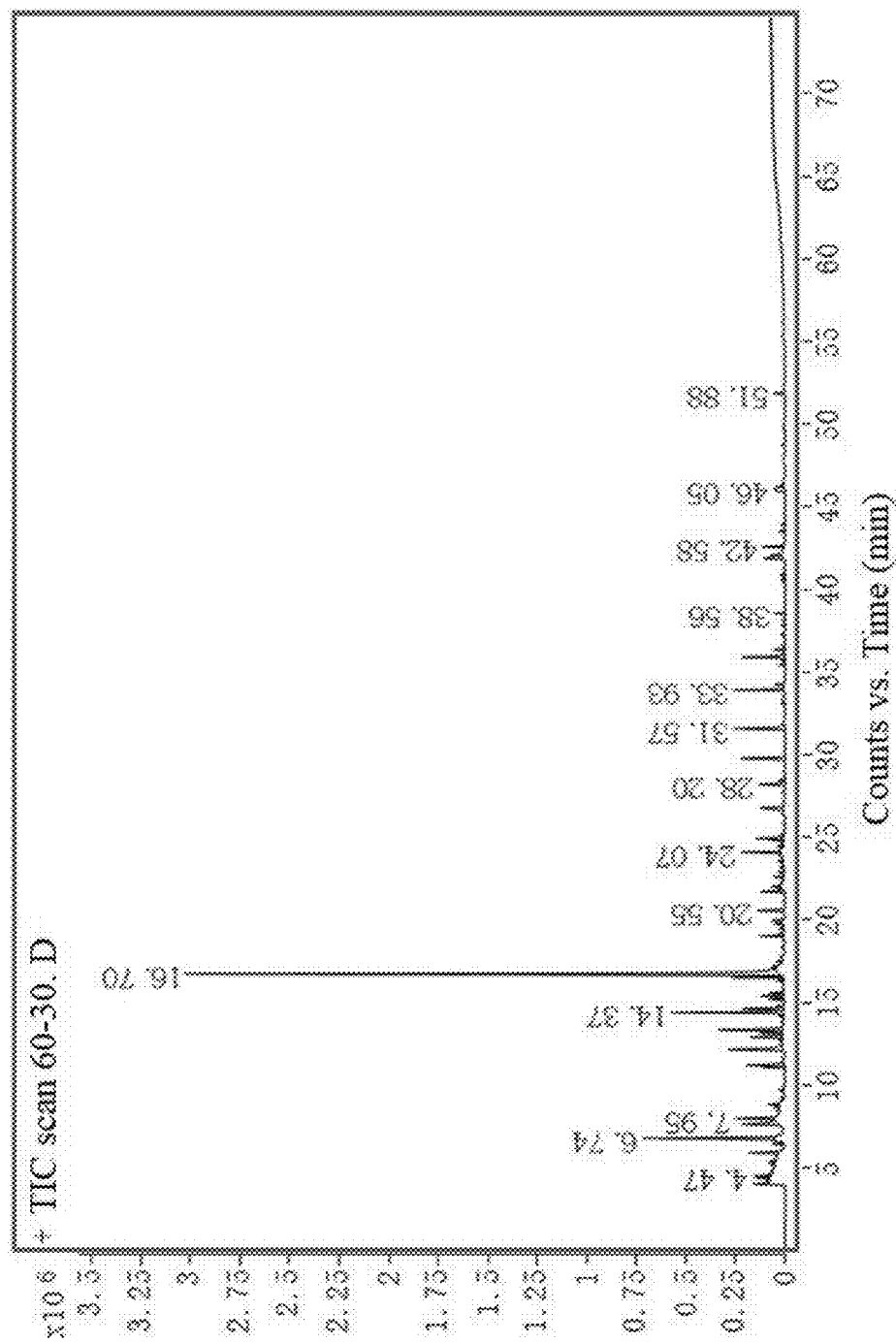

The TIC of the sample to be tested is shown in FIG. 14B. A prediction is based on the regression curve between the myofibrillar protein extraction ratio and the number of different types of volatile flavor substances. The types and amount of the volatile flavor substances in LTVH60-30 are shown in Table 2. The myofibrillar protein content calculated by the prediction model was 17.17123%, and the actual myofibrillar protein content was 17.17127% with a relative deviation of prediction being 0.00026%. This shows that the regression curve could accurately predict the myofibrillar protein extraction ratio of the sample to determine the degree of doneness.

TABLE 4

Types and amounts of volatile flavor substances in the sample in Example 2

| | LTVH50-15 | LTVH50-30 | LTVH60-30 | LTVH70-15 | LTVH70-30 | TC100-15 |
|---|---|---|---|---|---|---|
| Acetone | 1092.515 | 3166.211333 | 1351.545667 | 2301.943667 | 2713.151 | 3875.865667 |
| 2-butanone monomer | 833.609 | 1451.395 | 747.687 | 1040.750333 | 1099.156333 | 1282.438333 |
| Ethyl acetate monomer | 635.4893333 | 539.739 | 558.3936667 | 402.8853333 | 492.49 | 414.754 |
| Ethyl acetate dimer | 188.5713333 | 142.6596667 | 187.5213333 | 76.10566667 | 120.1766667 | 118.434 |
| 3-methylbutanal monomer | 555.6446667 | 558.217 | 275.336 | 262.0243333 | 388.5626667 | 711.0326667 |
| 3-methylbutanal dimer | 254.9526667 | 158.7236667 | 62.76 | 53.41633333 | 96.98366667 | 371.9613333 |
| Acetylacetone monomer | 1316.502667 | 534.3076667 | 928.03 | 1484.413333 | 1096.660667 | 1881.913667 |
| Acetyl dimer | 315.3886667 | 258.7856667 | 207.9383333 | 441.6536667 | 331.826 | 721.338 |
| Benzaldehyde | 156.3466667 | 274.7236667 | 141.395 | 149.5026667 | 167.2806667 | 151.2143333 |
| N-nonanal | 364.0623333 | 315.044 | 364.6003333 | 371.7013333 | 323.7786667 | 301.0543333 |
| Octanoic acid | 172.8633333 | 396.942 | 314.9603333 | 372.3293333 | 350.9216667 | 285.3846667 |
| Pentanal monomer | 430.192 | 1015.541 | 861.7086667 | 727.9783333 | 879.769 | 383.2993333 |
| Hexanal monomer | 1462.463333 | 2796.367667 | 2736.581667 | 2628.669333 | 2710.688333 | 2080.02 |
| Hexanal dimer | 829.22 | 5501.522 | 4556.180333 | 3197.962667 | 3930.321333 | 1767.170667 |
| Heptanal dimer | 59.59 | 220.8683333 | 148.9803333 | 98.40366667 | 107.1266667 | 64.89066667 |
| 1-hexanol dimer | 43.097 | 43.744 | 90.586 | 191.5953333 | 200.226 | 216.6623333 |
| Heptanal monomer | 417.7313333 | 1076.712 | 892.508 | 862.984 | 874.0033333 | 655.828 |
| 1-hexanol monomer | 73.35133333 | 99.75533333 | 414.8763333 | 683.6673333 | 684.4076667 | 705.0966667 |
| 3-octanol | 65.024 | 193.4856667 | 171.4526667 | 180.3263333 | 206.214 | 131.1853333 |
| 2-butanone dimer | 64.77933333 | 1087.649 | 165.296 | 415.128 | 652.547 | 1108.438333 |
| 2-heptanone | 46.48566667 | 89.10033333 | 78.43733333 | 87.34566667 | 78.67833333 | 74.84433333 |
| Pentanal dimer | 32.607 | 588.2113333 | 262.999 | 124.424 | 243.453 | 53.91366667 |
| 2-pentanone monomer | 63.09333333 | 35.60466667 | 62.51666667 | 79.578 | 59.499 | 77.68733333 |
| 2-pentanone dimer | 25.54 | 160.3286667 | 61.76633333 | 76.48933333 | 70.797 | 72.98033333 |
| Cyclohexanone | 35.36466667 | 195.4366667 | 56.81233333 | 58.00633333 | 69.797 | 48.689 |
| Predicted myofibrillar protein extraction ratio (%) | 29.99896 | 27.32501 | 17.17123 | 8.463198 | 4.850957 | 8.159824 |
| Actual myofibrillar protein extraction ratio (%) | 29.99899 | 27.32503 | 17.17127 | 8.463249 | 4.851009 | 8.159876 |
| Relative deviation of prediction (%) | 0.000122247 | 9.66431E−05 | 0.00026921 | 0.000606532 | 0.001063612 | 0.000639678 |

(9) Verification of Prediction Results

Figure 15B:
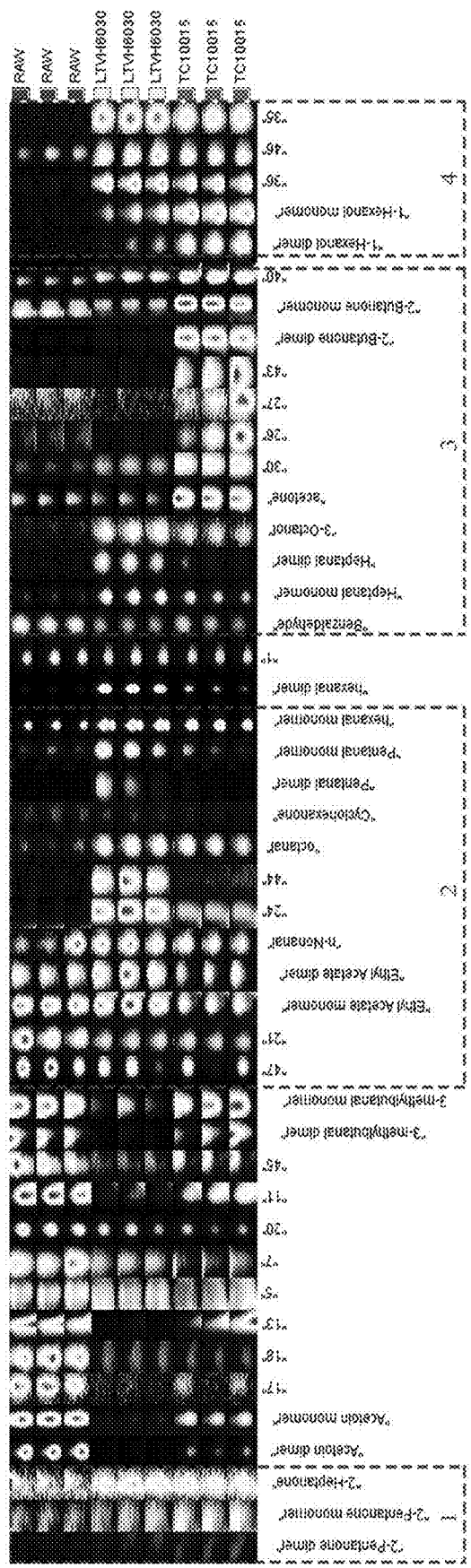

According to FIG. 15B, the fingerprints of the sturgeon meat treated at 60° C. for 30 min and other treatment groups were significantly different. In general, the types of the volatile flavor substances were closer to those of the TC treatment group, and the contents of the flavor substances were closer to those of the TC treatment group except for the 2-butanone in Region 3. This shows that GC-IMS could effectively distinguish the characteristic flavors of different samples to determine their degree of doneness.

The above embodiments are intended to explain the present disclosure, rather than to limit the present disclosure. Any modifications and changes made to the present disclosure within the spirit and the protection scope defined by the claims should all fall within the protection scope of the present disclosure.

What is claimed is:

1. A method for determining a degree of doneness of a sturgeon meat based on flavor fingerprinting and a partial least squares (PLS) regression, comprising the following steps:
   (1) shaping the sturgeon meat to a fixed size and heating the sturgeon meat at different temperatures at different times to obtain a heated sturgeon meat;
   (2) pulping the heated sturgeon meat in step (1) to obtain a pulped sturgeon meat; pipetting 11-15 mL of the pulped sturgeon meat into a first 20 mL headspace vial; sealing the first headspace vial; equilibrating the first headspace vial at 50-52° C. for 25-30 min; inserting an extraction head into the first headspace vial to allow adsorption at a distance of 1-2 cm from a liquid surface for 25-30 min; inserting the extraction head into a gas chromatography (GC) injection port desorbing at 235-245° C. for 2 min; and conducting a gas chromatography-mass spectrometry (GC-MS) analysis;
   (3) loading 1-5 g of the heated sturgeon meat in step (1) into a second 20 mL headspace vial; sealing the second headspace vial; incubating the second headspace vial at 45-55° C. for 15-25 min; and taking, by a syringe at 80-90° C., 490-510 μL of headspace gas from the second headspace vial for a gas chromatography-ion mobility spectrometry (GC-IMS) analysis;
   (4) measuring a myofibrillar protein content of the heated sturgeon meat in step (1), and calculating a myofibrillar protein extraction ratio indicating a ratio of a myofibrillar protein content of the heated sturgeon meat to a myofibrillar protein content of the sturgeon meat before heating;
   (5) establishing a multivariate linear fit curve by the PLS regression by taking the myofibrillar protein extraction ratio as a response variable and an amount of volatile flavor substances as independent variables, directly comparing characteristic regions of a fingerprint by GC-IMS, and conducting a principal component analysis (PCA); and
   (6) determining a degree of doneness of a target sturgeon meat sample by acquiring GC-MS and GC-IMS data of the target sturgeon meat sample, analyzing through the multivariate linear fit curve established in step (5), and comparing characteristic regions of a fingerprint of the target sturgeon meat sample and conducting the PCA according to step (5).

2. The method for determining the degree of doneness of the sturgeon meat based on flavor fingerprinting and the PLS regression according to claim 1, wherein step (1) further comprises: shaping a raw sturgeon meat to 3 cm×3 cm×1 cm and vacuum-heating at 50° C., 70° C., and 100° C. each for 15 min and 30 min, respectively.

3. The method for determining the degree of doneness of the sturgeon meat based on flavor fingerprinting and the PLS regression according to claim 1, wherein in the GC-MS analysis in step (2), a GC analysis is conducted by a chromatographic column comprising a splitless injection at an inlet temperature of 240° C. and a constant flow rate of 1 mL/min, and the GC analysis is subjected to a temperature programming: holding 35° C. for 3 min, raising the temperature to 220° C. at 3° C./min, and holding at 220° C. for 10 min; and an MS analysis is conducted by a 230° C. electron impact (EI) ion source and 150° C. quadrupoles with a mass range of 33-500 amu.

4. The method for determining the degree of doneness of the sturgeon meat based on flavor fingerprinting and the PLS regression according to claim 1, wherein in the GC-IMS analysis in step (3), a GC analysis is conducted by programming a flow rate of high-purity nitrogen (99%), wherein the high-purity nitrogen serves as a carrier gas: holding an initial flow rate of 2 mL/min for 2 min, and raising the flow rate to 10 mL/min at 10 min, 100 mL/min at 20 min, and 150 mL/min at 30 min; and an IMS analysis is conducted by controlling a flow rate of a drift gas at 150 mL/min.

5. The method for determining the degree of doneness of the sturgeon meat based on flavor fingerprinting and the PLS regression according to claim 1, wherein in step (4), the myofibrillar protein content is determined by using a Coomassie brilliant blue method; and the myofibrillar protein extraction ratio is calculated by $$A(\%) = \frac{P}{C} \times 100,$$

wherein A denotes the myofibrillar protein extraction ratio (%); P denotes the myofibrillar protein content of the heated sturgeon meat (mg/100 g); and C denotes the myofibrillar protein content of the sturgeon meat before heating (mg/100 g).

6. The method for determining the degree of doneness of the sturgeon meat based on flavor fingerprinting and the PLS regression according to claim 1, wherein in step (5), the multivariate linear fit curve between the myofibrillar protein extraction ratio and a number of different types of volatile flavor substances is expressed by: $Y=16.8553+0.0496382X_1-0.0167546X_2+0.0284132X_3-0.0359706X_4+0.0106525X_5-0.0796625X_6-0.0192646X_7+0.0360119X_8+0.0194102X_9+0.0196761X_{10}$, wherein $X_1$, $X_2$, $X_3$, $X_4$, $X_5$, $X_6$, $X_7$, $X_8$, $X_9$, and $X_{10}$ denote contents of 2-butanone monomer, ethyl acetate monomer, acetylacetone monomer, acetyl dimer, n-nonanal, octanoic acid, hexanal dimer, heptanal monomer, 1-hexanol monomer, and cyclohexanone, respectively.

7. The method for determining the degree of doneness of the sturgeon meat based on flavor fingerprinting and the PLS regression according to claim 1, wherein step (5) further comprises: conducting a comparative analysis of the fingerprint by GC-IMS to acquire characteristic regions of the volatile flavor substances, wherein the characteristic regions characterize a flavor characteristic of the sturgeon meat, and conducting a dynamic PCA by a Dynamic PCA plug-in to cluster volatile flavor substances and quickly determine a type of an unknown volatile flavor substance.

* * * * *